United States Patent [19]

Gibson

[11] 4,073,690
[45] Feb. 14, 1978

[54] CITROBACTER FREUNDII BROTH

[75] Inventor: Sandra F. Gibson, St. Louis, Mo.

[73] Assignee: McDonnell Douglas Corporation, St. Louis, Mo.

[21] Appl. No.: 682,654

[22] Filed: May 3, 1976

[51] Int. Cl.² .............................................. C12K 1/06
[52] U.S. Cl. .................................................. 195/100
[58] Field of Search .............................. 195/99–103, 195/103.5 R

[56] References Cited

PUBLICATIONS

Robert Bailey and Elvyn Scott, Diagnostic Microbiology; Second Ed., the C. V. Mosley Company, 1966, p. 26.

*Primary Examiner*—Lionel M. Shapiro
*Assistant Examiner*—Robert J. Warden
*Attorney, Agent, or Firm*—Gravely, Lieder & Woodruff

[57] ABSTRACT

A broth medium for the detection of *Citrobacter freundii* in urine. The medium employs palatinose and rhamnose as carbon sources to enhance the growth of the organism. A combination of α-hydroxy-2',4,4'-trichlorodiphenyloxide and Brilliant Green are employed to inhibit the growth of Aeromonas and Klebsiella organisms. Gram positive organisms are inhibited by surfactants, such as Bile Salts mixture. The presence of *C. freundii* is detected by means of precipitation and a consequent change in the light transmitting properties of the medium.

10 Claims, No Drawings

CITROBACTER FREUNDII BROTH

BACKGROUND OF THE INVENTION

*Citrobacter freundii* (*C. freundii*) is an organism which occurs in water, food, feces, and urine. The organism is throught to be found constantly in healthy persons. Certain serotypes apparently cause sporadic infections of alimentary and urinary tracts, and infections of gall bladder, middle ear, and meninges have been reported. The presence of this organism in urine is a reliable indicator of a urinary tract infection. If *C. freundii* is present in a given sample of urine, it is possible that Aeromonas and Klebsiella also are present.

The medium of this invention is an improved medium designed for use with the optical detection system disclosed in U.S. applications Ser. Nos. 255,533 filed May 22, 1972 now abandoned and 461,249 filed Apr. 16, 1974 now U.S. Pat. No. 3,963,355 and in the improved device disclosed and claimed in applications filed on even date herewith by Charles, Jones, Staples and Wiegner entitled AUTOMATED MICROBIAL ANALYZER and MACHINE AND PROCESS FOR READING CARDS CONTAINING MEDICAL SPECIMENS. These applications describe mechanism and apparatus suitable for analyzing specimens for specific microorganisms using a plastic tray or card which contains a series of dried culture media contained in separate but connected cells, each of the media being specific to a single organism. When the sample is inserted into the card, mixed with the media in the cells, and incubated in the machine, the organism (or organisms) present in the specimen interacts with the culture medium specific to that organism and produces a change in the medium which is read by the machine to indicate the presence of that organism. The change in the medium involves a change in the light transmitting properties of the medium, i.e., a color change or change in turbidity. The change may be caused by metabolic activity of the organisms, which, for example, may cause production of acid and a change in pH which causes a color change in a pH sensitive indicator in the medium. The change in the light transmitting properties of the medium also may be caused by a precipitate forming in the medium due to metabolic activity of the organism or it may be caused by growth of the organism.

The specific media designed for use in the aforesaid cards are all designed to favor growth of one microorganisms, are capable of being freeze dried, and can function in the low $O_2$ environment of the wells of the card described in detail in said copending applications AUTOMATED MICROBIAL ANALYZER and MACHINE AND PROCESS FOR READING CARDS CONTAINING MEDICAL SPECIMENS.

I have discovered a medium which can selectively identify *C. freundii* organism in urine when the medium is placed in the wells of the cards described in application AUTOMATED MICROBIAL ANALYZER.

Positive results are indicated by means of a precipitate formed in the clear medium which causes a change in the light transmitting character of the medium, which change is read by the mechanism described in application AUTOMATED MICROBIAL ANALYZER. The entire test can be completed within 8–12 hours, whereas current methods of detection require from about 36 to about 48 hours.

SUMMARY OF THE INVENTION

This invention involves a broth medium for the detection of *Citrobacter freundii* in urine.

The medium contains various nutrients, including palatinose and rhamnose, and various chemical inhibitors, including α-hydroxy-2',4,4'-trichloro-diphenyloxide, and Brilliant Green.

Among the novel aspects of this invention are the use of palatinose and rhamnose as nutrients which operate to selectively stimulate the growth of *C. freundii* and to precipitate bile salts from solution at an acid pH; the use of α-hydroxy-2',4,4'-trichloro-diphenyloxide as an inhibitor of growth of Klebsiella; and also the use of higher than normal amounts of Brilliant Green to inhibit the growth of Aeromonas, Shigella, etc. The presence of *C. freundii* is detected by precipitation of bile salts from the medium, which precipitation is caused by the pH of the medium becoming acid from the acid produced when the *C. freundii* ferments the palatinose or rhamnose.

DETAILED DESCRIPTION

The detection broth of the present invention contains from about 22.5 to about 27.5 gms/l nutrients (amino acids and carbohydrates); about 9 to about 11 gm/l Bile Salts Mixture, which operates as a biological inhibitor to inhibit the growth of gram-positive organisms which normally give positive results in tests for *C. freundii*; about 14.5 to about 15.5 ml/l α-hydroxy-2',4,4'-trichloro-diphenyloxide (in a 1% by weight solution), which operates to inhibit the growth of Klebsiella organisms; and about 52 to 55 mgm/l of Brilliant Green to inhibit the growth of Aeromonas, Shigella and like organisms.

The nutrient portion of the medium contains from about 4.5 to about 5.5 gm/l Gelysate (preferably about 5 gm/l), from about 9.0 to about 11.0 gm/l rhamnose (preferably about 10 gm/l), and from about 9.0 to about 11.0 gm/l palatinose (preferably about 10 gm/l).

A suitable substitute for Gelysate is Trypticase. Both of these are from BBL. Gelysate is a gelatine hydrolysate made by pancreatic digestion characterized by low cystine and tryptophane content.

Trypticase is made by BBL and is a peptone derived from casein by pancreatic digestion.

Bile Salts Mixture is from BBL and is used to inhibit the growth of gram-positive organisms. Bile Salts Mixture contains bile extractives and is a mixture of surfactants which inhibit gram-positive organisms, such as *S. aureus, enterococci*. Other suitable surfactants are sodium deoxycholate, cholic acid, deoxycholic acid, etc.

Palatinose is a sugar (carbon source) used to enhance the growth of *C. freundii*. Palatinose is fermented by *C. freundii* to produce an acid which causes the medium to change pH. When the starting pH of 7.5 has become acid, i.e. pH less, a precipitate is formed from the solution which changes the light transmitting characteristics thereof, which change is observed and recorded by the mechanism described in application AUTOMATED MICROBIAL ANALYZER.

Rhamnose is a sugar and is fermented by a small percentage of *C. freundii* organisms which do not utilize palatinose. When rhamnose is fermented, acid is produced and the medium acts as described for palatinose. Palatinose is not generally used as a nutrient for *C. freundii* and stimulates growth of several strains of *C.*

*freundii* that would not normally grow in a conventional *C. freundii* growth medium.

Sodium hydroxide is used to adjust the pH of the medium to 7.5.

α-hydroxy-2',4,4'-trichloro-diphenyloxide acts to inhibit growth of Klebsiella organisms, which yield false positive test results in the conventional *C. freundii* detection methods.

The concentration of α-hydroxy-2',4,4'-trichloro-diphenyloxide can be from about 14.5 ml of a 1% solution per liter of medium to about 15.5 ml of 1% solution per liter of medium. The preferred concentration and the most effective is 15 ml of 1% solution per liter of medium. If the concentration of any inhibitor is too low, a higher yield of unwanted false positives occurs. If the concentration is too high, a lower yield of positives occurs.

Brilliant Green is used as an inhibitor for Aeromonas, Shigella, and other organisms. The Brilliant Green is used in higher concentrations than normal and can be in the range of about 52 mgm to about 55 mgm/l of medium. It preferably is used at about 53.2 mgm/l of medium.

EXAMPLE I

To prepare a 2 × medium in an amount of 100 ml, *C. freundii* detection broth is prepared by thoroughly mixing the following components in the specified amounts:
    Trypticase: 1 gm
    Bile Salts Mixture: 2 gm
    Palatinose: 2 gm
    Rhamnose: 2 gm
    Distilled Water: 92 ml The foregoing ingredients are stirred and 8 ml of Brilliant Green stock solution is added. This contains 0.133 gm % solids.

In a separate container 1 gm of α-hydroxy-2',4,4'-trichloro-diphenyloxide is mixed with 90 ml distilled water and 10 ml 1N NaOH and heated until dissolved to produce a stock solution. 3 ml of the foregoing stock is added to the nutrient composition, the pH is adjusted to 7.5 by means of sodium hydroxide, and the composition is filter sterilized.

The medium is at double (2×) the usual concentration for use in the wells and card described in application entitled AUTOMATED MICROBIAL ANALYZER.

What is claimed is:

1. A broth medium for selective identification of *Citrobacter freundii* comprising:
    a. a source of nutrients including at least one sugar that specifically enhances the growth of *C. freundii* and is fermentable by *C. freundii* to acidify the said broth, said sugars being selected from palatinose, rhamnose, and combinations thereof,
    b. a gram-positive inhibitor, and
    c. an inhibitor to inhibit the growth of organisms that give false positive results in tests for *C. freundii*,
    d. said broth medium being responsive to a pH change toward and induced by said sugar fermentation by *C. freundii* to indicate the presence of *C. freundii* in said broth.

2. The medium of claim 1 wherein about 9 to about 11 gm/l palatinose is used.

3. The medium of claim 1 including a source of amino acids in the nutrient portion of the medium.

4. The medium of claim 3 including Trypticase as the amino acid source.

5. The medium of claim 1 wherein the false positive inhibitor is α-hydroxy-2',4,4'-trichloro-diphenyloxide.

6. The medium of claim 5 wherein the equivalent of about 14.5 to about 15.5 gm/l of medium of a 1% solution of α-hydroxy-2',4,4'-trichloro-diphenyloxide is included as an inhibitor.

7. The medium of claim 1 wherein the gram positive inhibitor is Bile Salts Mixture.

8. The medium of claim 1 containing *C. freundii* and a precipitate produced by the presence of said *C. freundii*.

9. The medium of claim 1 comprising per liter of medium:
    A. about 4.5 to about 5.5 gms amino acid source,
    B. about 9 to about 11 gms surfactants,
    C. about 9 to about 11 gms palatinose,
    D. about 9 to about 11 gms rhamnose,
    E. about 52 to about 55 mg Brilliant Green, and
    F. the equivalent of about 14.5 to about 15.5 ml of a 1% solution of α-hydroxy-2',4,4'-trichloro-diphenyloxide, and
    G. distilled water,
    H. the medium being at a pH of about 7.5.

10. The medium of claim 1 comprising per liter of medium:
    A. about 5 gm Gelysate,
    B. about 10 gm Bile Salts Mixture,
    C. about 10 gm palatinose,
    D. about 10 gm rhamnose,
    E. about 53 mgm Brilliant Green,
    F. the equivalent of about 15 ml of a 1% solution of α-hydroxy-2',4,4'-trichloro-diphenyloxide, and
    G. distilled water.

* * * * *